US010869919B2

(12) United States Patent
Tian et al.

(10) Patent No.: US 10,869,919 B2
(45) Date of Patent: Dec. 22, 2020

(54) PORCINE CIRCOVIRUS TYPE 3 STRAIN, VACCINE COMPOSITION, METHOD OF MAKING THE SAME AND USE THEREOF

(71) Applicant: PULIKE BIOLOGICAL ENGINEERING, INC., Henan (CN)

(72) Inventors: Kegong Tian, Henan (CN); Xiangdong Li, Henan (CN); Yan Xiao, Henan (CN); Jinzhong Sun, Henan (CN); Xuke Zhang, Henan (CN)

(73) Assignee: PULIKE BIOLOGICAL ENGINEERING, INC., Henan (CN)

( * ) Notice: Subject to any disclaimer, the term of this patent is extended or adjusted under 35 U.S.C. 154(b) by 0 days.

(21) Appl. No.: 16/483,941

(22) PCT Filed: Nov. 30, 2017

(86) PCT No.: PCT/CN2017/113945
§ 371 (c)(1),
(2) Date: Aug. 6, 2019

(87) PCT Pub. No.: WO2018/176887
PCT Pub. Date: Oct. 4, 2018

(65) Prior Publication Data
US 2019/0388533 A1    Dec. 26, 2019

(30) Foreign Application Priority Data
Mar. 29, 2017   (CN) .......................... 2017 1 0198414

(51) Int. Cl.
| | |
|---|---|
| *A61K 39/12* | (2006.01) |
| *A61P 31/20* | (2006.01) |
| *C12N 7/00* | (2006.01) |
| *A61K 39/00* | (2006.01) |

(52) U.S. Cl.
CPC .............. *A61K 39/12* (2013.01); *A61P 31/20* (2018.01); *C12N 7/00* (2013.01); *A61K 2039/5252* (2013.01); *A61K 2039/552* (2013.01); *C12N 2750/10021* (2013.01); *C12N 2750/10034* (2013.01)

(58) Field of Classification Search
CPC .............. A61K 39/12; A61K 2039/552; A61K 2039/5252; A61K 2039/53; A61K 2039/525; C12N 2750/10034; C12N 2750/10022; C12N 7/00; C12N 2750/10021; C12N 2750/10033; C12N 2750/10032; C12N 2750/10031; C12N 2750/10023; C07K 14/005; C07K 16/081; C07K 14/01
See application file for complete search history.

(56) References Cited

FOREIGN PATENT DOCUMENTS

| CN | 105087501 A | 11/2015 |
|---|---|---|
| WO | 2017/066772 A1 | 4/2017 |

OTHER PUBLICATIONS

Fenaux M, Opriessnig T, Halbur PG, Elvinger F, Meng XJ. Two amino acid mutations in the capsid protein of type 2 porcine circovirus (PCV2) enhanced PCV2 replication in vitro and attenuated the virus in vivo. J Virol. Dec. 2004;78(24):13440-6.*
Beek V T, "Scientists Describe Porcine Circovirus, Type 3", PigProgress (Feb. 22, 2017).
D.T.L. "Porcine Circovirus 3", SHIC, pp. 1-16 (Sep. 30, 2016).
Fan S. et al., "Complete Genome Sequence of a Novel Porcine Circovirus Type 3 Strain, PCV3/CN/Hubei-618/2016, Isolated from China", American Society for Microbiology 5(15):e00100-17 (Apr. 13, 2017).
Palinski R. et al., "A Novel Porcine Circovirus Distantly Related to Known Circoviruses is Associated With Porcine Dermatitis and Nephropathy Syndrome and Reproductive Failure", Journal of Virology 91(1):e01879-16 (Oct. 26, 2016).
Phan T.G. et al., "Detection of a Novel Circovirus PCV3 in Pigs With Cardiac and Multi-Systemic Inflammation", Virology Journal 13:184, pp. 1-8 (Nov. 11, 2016).
International Search Report dated Jan. 25, 2018 received in International Application No. PCT/CN2017/113945, together with an English-language translation.
Pang, P. et al., "Conception of Evaluation System for Efficacy of PCV2 Vaccination", Journal of Economic Animal, vol. 20, No. 2, pp. 118-124, together with English language abstract (Jun. 2016). Cited in Search Report of Chinese Patent Application No. 201710198414.3.
Zhang, Z. et al., "Diagnosis and Prevention of Circovirus in a pig farm", Swine Production, Issue 4, pp. 113-115, together with English language abstract (2014). Cited in Search Report of Chinese Patent Application No. 201710198414.3.
International Preliminary Report on Patentability dated Oct. 10, 2019, together with the Written Opinion received in related International Application No. PCT/CN2017/113945, together with an English language translation.

* cited by examiner

*Primary Examiner* — Rachel B Gill
(74) *Attorney, Agent, or Firm* — Scully Scott Murphy & Presser

(57) ABSTRACT

A porcine circovirus type 3 virus strain and a vaccine composition prepared from the immunogenic substance of the strain are described. The porcine circovirus type 3 virus strain has good immunogenicity, and the prepared vaccine composition can provide complete protection against varies of porcine circovirus type 3 viruses from different sources.

12 Claims, No Drawings

PORCINE CIRCOVIRUS TYPE 3 STRAIN, VACCINE COMPOSITION, METHOD OF MAKING THE SAME AND USE THEREOF

FIELD OF THE INVENTION

The disclosure relates to a strain, a vaccine composition prepared therefrom, a method of making the same and a use thereof, belonging to the field of animal virology.

BACKGROUND

A porcine circovirus (PCV) is a single-stranded DNA virus with a length of genomic sequence of about 1.7 kb, making it one of the smallest animal DNA viruses. Two types of PCV have been identified, namely porcine circovirus type 1 (PCV1) and porcine circovirus type 2 (PCV2). PCV1, which was first identified in PK cell culture as a contaminant in 1974, is not pathogenic to pigs. PCV2 first reported in 1998 can cause porcine circovirus associated diseases (PCVAD) in pigs under clinical conditions, mainly causing piglet multisystemic wasting syndrome, pneumonia, porcine dermatitis and nephropathy syndrome, of which manifestations include respiratory dysfunction, urinary dysfunction, intestinal dysfunction, lymphatic dysfunction, cardiovascular dysfunction, neurological dysfunction, reproductive system dysfunction and skin dysfunction, which has caused significant economic losses to pig farming worldwide.

However, in a case of reproductive failure in pigs, a porcine circovirus strain with a length of genomic sequence of 2.0 kb was isolated and confirmed as the pathogenic pathogen. As further confirmed by subsequent experiments, the sequence of the strain shared less than 50% identity at the nucleotide- or amino acid-level (nt- or aa-level) to those of any reported circoviruses. According to the standard from the International Committee on Taxonomy of Viruses, ICTV, members of the genus Circovirus should share >75% nt-identity over their entire genome, and >70% aa-identity in the Cap protein. It is therefore confirmed as a new species in the genus Circovirus. It can cause porcine dermatitis and nephrophathy syndrome, reproductive disorders, and inflammatory responses to the heart and multiple systems, so the preparation of new vaccines with respect to this new virus is very important for disease control in pig farms.

SUMMARY OF THE INVENTION

In order to solve the deficiencies of the prior art, the present disclosure provides a vaccine composition for preventing and/or treating infection by a new porcine circovirus, the vaccine composition can provide effective protection against the new porcine circovirus exhibiting significant immunological properties.

To this end, it is an object of the present disclosure to provide a porcine circovirus type 3 strain SG strain, from which a vaccine composition prepared can effectively prevent the attack of the epidemic strain, and provides complete protection against porcine circovirus type 3 strains from different sources.

Another object of the present disclosure is to provide a vaccine composition for preventing and/or treating infection by a new porcine circovirus, the vaccine composition comprises an immunogenic amount of inactivated antigen of porcine circovirus type 3 SG strain and culture thereof, and a carrier.

Another object of the present disclosure is to provide a method for preparing an inactivated porcine circovirus type 3 vaccine, comprising: step (1) proliferating the porcine circovirus type 3 SG strain; step (2) inactivating said proliferated porcine circovirus type 3 SG strain from step (1) which is then added with an adjuvant and emulsified.

Another object of the present disclosure is to provide a use of the above vaccine composition in preparing medicine for prevention and/or treatment of porcine circovirus type 3 related diseases.

Advantages of the disclosure:
(1) The SG strain of the present disclosure has good immunogenicity, can stimulate the body to rapidly produce immunity, and effectively prevent the attack of the epidemic strain, providing a good protective effect;
(2) The present disclosure is the first to prepare the vaccine composition by the new porcine circovirus type 3 strain, the vaccine composition can achieve better immune protective effect at lower antigen content and further reduce cost of production; (3) The vaccine of the present disclosure can provide complete protection against porcine circovirus type 3 strains of different regions, and have an ability to provide broad-spectrum protection;
(4) The vaccine of the present disclosure can provide a therapeutic effect on pigs that have been infected with porcine circovirus type 3 virus and exhibited initial clinical symptoms.

DETAILED DESCRIPTION

Hereinafter, embodiments of the present disclosure will be described.

Porcine circovirus type 3 is a porcine circovirus with a length of genomic sequence of 2.0 kb, the sequence of which shares less than 50% identity at the nt- or aa-level to those of any reported circoviruses and is a new species of porcine circovirus. It can cause porcine dermatitis and nephrophathy syndrome, reproductive disorders, and inflammatory responses to the heart and multiple systems.

An object of the present disclosure is to provide a porcine circovirus type 3 SG strain deposited in the China Center for Type Culture Collection on Mar. 23, 2017, of which the accession number is CCTCC NO. V201712 and the address is Wuhan University, Wuhan, China.

The vaccine composition prepared for porcine circovirus type 3 may comprise an immunogenic amount of inactivated antigen, attenuated whole virus antigen, subunit antigen or synthetic peptide antigen, autonomously replicable vector containing a gene encoding a subunit antigen protein of porcine circovirus type 3 or a culture thereof, and a pharmaceutically acceptable carrier.

The "culture" refers to cultures of different passages of the virus, known to those skilled in the art, which may only have minute variations in gene sequences from one passage to another.

The "vaccine composition" refers to a pharmaceutical composition having immunogenicity against porcine circovirus type 3. The pharmaceutical composition can induce, stimulate or enhance the immune response of pigs to porcine circovirus type 3.

The "inactivated vaccine", also called non-living vaccine, refers to suspension of inactivated virus used as an antigen for producing immunity. Examples of inactivated vaccines include whole-virus vaccines and split-virus vaccines. By using known methods it is easy to produce inactivated vaccines. For instance, one can obtain inactivated whole-virus vaccines by treatment with formaldehyde solution. Split-virus vaccines can be prepared with virus envelopes after treatment with ether.

"Attenuated whole-virus antigen" refers to a virus which still can reproduce in the host or on the cells while their virulence has been weakened. As used herein, the term "attenuated" refers to artificially reducing the virulence of pathogens via mutation of gene by preparing pathogens which are deprived of pathogenicity but maintain immunogenicity. Generally attenuation can be achieved by UV irradiation, chemical processing or continuous high-order subculturing in vitro. Artificial alteration of gene attenuates the virulence via, for example, the deletion of some specific nucleotides in the given sequence.

"Subunit antigen" refers to an antigen prepared by genetically engineering a protective antigen gene of a pathogen into a prokaryotic or eukaryotic expression system for efficient expression. It is less likely to cause side effects than whole-virus antigens.

The "subunit antigen" refers to an antigen that is prepared by genetically engineering a protective antigen gene of a pathogen into a prokaryotic or eukaryotic expression system for highly efficient expression. It is less likely to cause side effects compared to the whole-virus antigens.

The "synthetic peptide antigen" refers to a small peptide that contains only a component of an immunological determinant, that is, an antigen that is prepared by synthesizing a protective short peptide according to the amino acid sequence of a natural protein by an artificial method, linking this protective short peptide with a vector, and adding an adjuvant.

The "autonomously replicable vector containing a gene encoding a subunit antigen protein" means that a non-pathogenic microorganism is genetically engineered to carry and express an antigen or antigenic determinant gene to produce immunogenicity; or a foreign gene encoding foreign protein of an antigenic protein is directly introduced into animals, and the antigenic protein is synthesized by the expression system of the host cell, thereby inducing the host to generate an immune response to the antigenic protein for the purpose of prevention and treatment.

The autonomously replicable vector containing a gene encoding a subunit antigen protein may be a live vector or a plasmid.

The "live vectors" refers to non-pathogenic microorganisms which carry and express a gene of an antigenic or antigenic determinant by mean of genetic engineering as to produce immunogenicity. The non-pathogenic microorganisms may be bacteria and viruses, viruses that are often used as viral live vectors include vaccinia virus, fowlpox virus, turkey herpes virus, adenovirus, pseudorabies virus, retrovirus, lentivirus; bacterial live vectors may include attenuated *Salmonella*, BCG, attenuated *Listeria monocytogenes*, attenuated *Vibrio cholerae*, attenuated *Shigella, Lactococcus lactis, Lactobacillus plantarum*, and *Streptococcus gordonii*.

The "plasmid" refers to a eukaryotic expression vector containing a gene encoding a foreign antigen, which has a specific promoter to initiate the foreign gene to be expressed at high levels in animals, and has various types, but mostly based on PUC or pBR322. These vectors all have elements such as an enhancer, a promoter, a vector selection marker, a sequence for translation initiation, a sequence for transcription termination, and a PolyA etc, the foreign antigen gene thereon can induce the body to produce protective immunity.

The present disclosure relates to a vaccine composition, wherein the vaccine composition comprises an immunogenic amount of inactivated antigen, attenuated whole-virus antigen, subunit antigen or synthetic peptide antigen, autonomously replicable vector containing a gene encoding a subunit antigen protein of porcine circovirus type 3 SG strain or a culture thereof, and a pharmaceutically acceptable carrier.

The present disclosure relates to a vaccine composition, wherein the vaccine composition comprises an immunogenic amount of porcine circovirus type 3 SG strain or a culture thereof, and a pharmaceutically acceptable carrier.

As an embodiment of the present disclosure, in the vaccine composition of the present disclosure, the inactivated antigen of the porcine circovirus type 3 SG strain or the culture thereof is an inactivated whole-virus antigen of the porcine circovirus type 3 virus SG strain.

The amount of the ingredient or component of the composition of the disclosure is preferably a therapeutically effective amount. The therapeutically effective amount refers to the amount necessary to exert the immunological effects of the composition in the host to which the composition is administered without causing excessive side effects. The precise amount of ingredients used and compositions to be administered will vary depending on factors such as the type of disease being treated, the type and age of the animal to be treated, the mode of administration, and other ingredients in the composition.

As an embodiment of the present disclosure, the inactivated whole-virus antigen content of the porcine circovirus type 3 SG strain or the culture thereof is equal to or more than $10^{5.0}$ TCID$_{50}$/ml before inactivation.

When porcine circovirus type 3 is used in an amount less than $10^{5.0}$ TCID$_{50}$/ml, the vaccine is not effective in stimulating production of antibody. On the other hand, the excess may be uneconomical.

As a preferred embodiment of the present disclosure, the inactivated whole-virus antigen content of the porcine circovirus type 3 SG strain or the culture thereof is within a range of $10^{5.0}$ to $10^{7.0}$ TCID$_{50}$/ml before inactivation.

As a more preferred embodiment of the present disclosure, the inactivated whole-virus antigen content of the porcine circovirus type 3 SG strain or the culture thereof is $10^{6.0}$ TCID$_{50}$/ml before inactivation.

In the vaccine composition of the present disclosure, the range of the inactivated whole-virus antigen content of the porcine circovirus type 3 SG strain or the culture thereof may further be selected from a range of $10^{5.0}$ to $10^{6.0}$ TCID$_{50}$/ml, or a range of $10^{6.0}$ to $10^{7.0}$ TCID$_{50}$/ml.

According to an embodiment of the present disclosure, in the vaccine composition, the culture of the porcine circovirus type 3 SG strain is a culture which has been subcultured for more than one passage.

According to a preferred embodiment of the present disclosure, in the vaccine composition, the culture of the porcine circovirus type 3 SG strain is a culture which has been subcultured for more than five passages.

According to a more preferred embodiment of the present disclosure, in the vaccine composition, the culture of the porcine circovirus type 3 SG strain is a culture which has been subcultured for 5 to 55 passages.

As an embodiment of the present disclosure, in the vaccine composition of the present disclosure, the pharmaceutically acceptable carrier includes an adjuvant, and the adjuvant includes (1) aluminum hydroxide, saponins, Avridine, DDA, (2) the polymers of acrylic or methaciylic acid, the copolymers of maleic anhydride and alkenyl derivative, (3) oil-in-water emulsion, water-in-oil emulsion, water-in-oil-in-water emulsion, or (4)) MontanideTMGel.

As a preferred embodiment of the present disclosure, in the vaccine composition of the present disclosure, the adjuvant includes (1) saponins e.g., Quil A; (2) carbomer in which the polymers of acrylic or methacrylic acid which are cross-linked, with polyalkenyl ethers of sugars or polyalcohols; (3) emulsion based in particular on light liquid paraffin oil; isoprenoid oil such as squalane or squalene oil resulting from the oligomerization of alkenes, in particular of isobutene or decene; esters of acids or of alcohols containing a linear alkyl group, more particularly plant oils, ethyl oleate, propylene glycol di- (caprylate/caprate), glyceryl tri- (caprylate/caprate) or propylene glycol dioleate; esters of branched fatty acids or alcohols, in particular isostearic acid esters; the emulsifiers are nonionic surfactants, in particular esters of Polyoxyethylene fatty acid (e.g. oleic acid), of sorbitan, of mannide (e.g. anhydromannitol oleate), of glycol, of polyglycerol. of propylene glycol and of oleic, isostearic, ricinoleic or hydroxy-stearic acid, which are optionally ethoxylated, ethers of fatty alcohols and polyhydric alcohols (e.g. oleyl alcohol) and polyoxypropylene-polyoxyethylene block copolymers, in particular the Pluronic® products, especially L121; or (4) Montanide™ Gel.

Preferably, the adjuvant is Montanide™ Gel, and the adjuvant is used in an amount of 5 to 20% by volume; more preferably, the adjuvant is used in an amount of 10% by volume.

The adjuvant includes white oil, oil Drake, and other animal oils, vegetable oils or mineral oil; or aluminum hydroxide, aluminum phosphate, and other metal salts; or Montanide™ Gel, carbomer, squalane or squalene, ISA206 adjuvant, saponin, oil emulsion, oil in water emulsions, water-in-oil emulsion.

Preferably, the adjuvant is Montanide™ Gel, and the adjuvant is used in an amount of 5 to 20% by volume; more preferably, the adjuvant is used in an amount of 10% by volume.

The adjuvant includes white oil, oil Drake, and other animal oils, vegetable oils or mineral oil; or aluminum hydroxide, aluminum phosphate, and other metal salts; or Montanide™ Gel, carbomer, squalane or squalene, ISA206 adjuvant, saponin, oil emulsion, oil in water emulsion, water-in-oil emulsion.

Vaccine compositions of the disclosure may be formulated using available techniques, preferably together with a veterinarily acceptable carrier. For example, oil can help to stabilize the formulation, and additionally act as a vaccine adjuvant. Oil adjuvants can be either naturally or synthetically obtained. The term "adjuvant" refers to a substance that is added to the composition of the present disclosure to increase the immunogenicity of the composition. Known adjuvants include, but are not limited to, (1) aluminum hydroxide, saponine (eg QuilA), Avridine, DDA, (2) the polymers of acrylic or methaciylic acid, the copolymers of maleic anhydride and alkenyl derivative, (3) oil-in-water emulsion, water-in-oil emulsion, water-in-oil-in-water emulsion, or (4)) MontanideTMGel.

In particular, the emulsion can be based in particular on light liquid paraffin oil; isoprenoid oil such as squalane or squalene oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri- (caprylate/caprate) or propylene glycol dioleate; esters of branched fatty acids or alcohols, in particular isostearic acid esters; the emulsifiers are nonionic surfactants, in particular esters of Polyoxyethylene fatty acid (e.g. oleic acid), of sorbitan, of mannide (e.g. anhydromannitol oleate), of glycol, of polyglycerol. of propylene glycol and of oleic, isostearic, ricinoleic or hydroxy-stearic acid, which are optionally ethoxylated, ethers of fatty alcohols and polyhydric alcohols (e.g. oleyl alcohol) and polyoxypropylene-polyoxyethylene block copolymers, in particular the Pluronic® products, especially L121 (See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997).).

In particular, adjuvant compounds are the polymers of acrylic or methacrylic acid which are cross-linked, with polyalkenyl ethers of sugars or polyalcohols. These compounds are known by the term carbomer.

Preferably, the adjuvant selected in the present disclosure is Montanide™ Gel.

The amount of adjuvant that is suitable for the composition of the present disclosure is preferably an effective amount. The "effective amount" refers to a required amount of the adjuvant that is necessary or sufficient to exert an immunological effect in the host in combination with the antigen of the disclosure without causing excessive side effects. The precise amount of adjuvant to be administrated varies depending on factors such as the components employed and the type of diseases being treated, the type and age of the animal to be treated, the mode of administration, and other ingredients in the composition.

The present disclosure also relates to a method of preparing the vaccine composition, wherein the method comprises: step (1) proliferating the porcine circovirus type 3 SG strain or a culture thereof; and step (2) inactivating said proliferated porcine circovirus type 3 SG strain or the culture thereof from step (1) and adding an adjuvant into the inactivated porcine circovirus type 3 SG strain or the culture thereof and emulsifying the resulting mixture.

The present disclosure may further incorporate additional agents into the compositions of the present disclosure. For example, the composition of the present disclosure may further comprise the following agents, such as: drugs, immunostimulants (e.g. α-interferon, β-interferon, γ-interferon, granulocyte-macrophage colony stimulating factor (GM-CSF), macrophage colony stimulating factor (M-CSF) and interleukin 2 (IL2)), antioxidants, surfactants, colorants, volatile oils, buffers, dispersants, propellants and preservatives. To prepare such compositions, methods well known in the art can be used.

The vaccine composition according to the disclosure may be prepared as an oral dosage form or a parenteral dosage form.

Preferred are parenteral dosage forms which can be administered via intradermal, intramuscular, intraperitoneal, intravenous, subcutaneous, intranasal or epidural routes.

The present disclosure also relates to a use of the above vaccine composition in preparing medicine for prevention and/or treatment of porcine circovirus type 3 related diseases.

The term "porcine circovirus type 3 related disease" as used in the present disclosure refers to a disease caused by infection of porcine circovirus type 3. Non-exhaustive examples include, but are not limited to, porcine dermatitis and nephrophathy syndrome, reproductive disorders, and inflammatory responses to the heart and multiple systems.

The term "prevention" as used in the present disclosure refers to all behaviors to inhibit the infection of porcine circovirus type 3 or delay the onset of the disease via administration of the vaccine composition according to the present disclosure. The term "treatment" refers to all behaviors to relieve or cure the symptoms caused by infection of porcine circovirus type 3 via administration of the vaccine composition according to the present disclosure.

Example 1 Isolation and Identification of Porcine Circovirus Type 3

1. Source of Tissue Sample

In a domestic commercial farm, compared with the historical average values, the sow mortality rate increased by 9.4%, the conception rate decreased by 1.2%, and the rate of mummified fetuses was increased by 8.2%. Clinically, the affected sows showed symptoms of anorexia, multifocal papules, spots and dermatitis on the skin surface. Mummified fetuses of different gestational ages were found for aborted sows, which are consistent with the symptoms of PCV2-related abortion. Although the overall clinical manifestations and abortion symptoms observed in sows were consistent with reproductive failure caused by porcine circovirus type 2, the results of immunohistochemical analysis and quantitative PCR for different tissues of all the sows, including kidney, lymph nodes, lungs, skin, and stillbirth, passed the immunization group were negative for PCV2, PRRSV, PPV, CSFV, and Mycoplasma hyopneumoniae. In order to further find out the reasons, the sample of each tissue were selected for isolation of pathogens.

2. Isolation and Cultivation of Virus Strains

The tissue sample was added to DMEM medium at a ratio of 1:10 (by volume), and grounded to prepare tissue suspension. The tissue suspension was centrifuged at 12000 r/min for 15 min after three repeated freeze-thaw cycles, and the supernatant was collected. After filtration of the supernatant through a 0.22 μm filter, the filtrate was passaged on PK15 cells, cultured at 37° C. for 1 h, then the culture medium was replaced with DMEM medium containing 2% of Newborn Calf Serum, and cultured at 37° C. for 5 days. The virus-containing culture solution was harvested, and after two freeze-thaw cycles, the virus was harvested.

3. Identification of Virus Species by PCR and Sequencing Analysis

The virus culture of the above step was taken, and the nucleic acid of the virus sample was extracted with a nucleic acid extraction kit, and PCR amplification was performed using a circovirus-specific primer. The result showed that a 2000 bp target band was amplified by PCR. The PCR product was sent to a sequencing company for determination of nucleotide sequence, and the result of sequencing was subjected to phylogenetic analysis. The results showed that both of the whole genome sequence and the amino acid sequence of the strain shared less than 50% identity to those of any other reported circoviruses. According to the standard from the International Committee on Taxonomy of Viruses, ICTV, members of the genus Circovirus should share >75% nt-identity over their entire genome, and >70% aa-identity in the Cap protein. It is therefore confirmed as a new species in the genus Circovirus, and the third type of circovirus found on pigs.

Example 2 Screening of Porcine Circovirus Type 3 Vaccine Strain

Specific primers were designed according to the above-mentioned isolated porcine circovirus type 3. By quantitative PCR analysis of 235 samples suspected to be positive for PCV3 collected from all over the country, 121 strains of PCV3 viruses were screened and isolated. Among these 121 strains, the identity of genomic nucleotide sequence was as high as 98.9~99.6%, and the identity of amino acid sequence of Cap protein was as high as 97.7~99.5%. After the animal pathogenicity test and immunogenicity test, a strain of PCV3 strain with strong pathogenicity, good immunogenicity and broad protective ability was screened out. This strain of porcine circovirus type 3 was named porcine circovirus type 3 SG strain and submitted for deposition.

Example 3 Pathogenicity Test of Porcine Circovirus Type 3 SG Strain 10 healthy piglets negative for PCV2, PCV3 antigen and antibody by ELISA, which were 28-30 days old, were randomly divided into two groups, 5 piglets/group, and the first group was challenged with PCV3 SG strain (including $10^{5.0}$ TCID$_{50}$/piglet), by intramuscular injection; the blank control group was inoculated with DMEM medium, and the piglets of each group were kept in isolation. After the challenge, the piglets in each group were continuously observed and evaluated according to their clinical symptoms, pathological changes and detection of virus. The detailed results are shown in Table 1.

TABLE 1

Results of pathogenicity test of porcine circovirus type 3 SG strain

| Group | No. | Clinical symptoms | Pathological changes | Detection of virus | Incidence rate |
|---|---|---|---|---|---|
| 1 | 1A | Temperature increased to above 40.5° C. for 5 days, loss of appetite, depression, rough hair coat, emaciation and low growth rate | Lung consolidation, lymphadenopathy, and kidney necrosis | Positive | 100% (5/5) |
|   | 1B | Temperature increased to above 40.5° C. for 3 days, loss of appetite, depression, rough hair coat, emaciation and low growth rate | Lung consolidation, lymphadenopathy, and kidney necrosis | Positive |   |
|   | 1C | Temperature increased to above 40.5° C. for 3 days, loss of appetite, depression, rough hair coat, emaciation and low growth rate | Lung consolidation, lymphadenopathy, and kidney necrosis | Positive |   |

TABLE 1-continued

Results of pathogenicity test of porcine circovirus type 3 SG strain

| Group | No. | Clinical symptoms | Pathological changes | Detection of virus | Incidence rate |
|---|---|---|---|---|---|
| | 1D | Temperature increased to above 40.5° C. for 4 days, loss of appetite, depression, rough hair coat, emaciation and low growth rate | Lung consolidation, lymphadenopathy, and kidney necrosis | Positive | |
| | 1E | Temperature increased to above 40.5° C. for 5 days, loss of appetite, depression, rough hair coat, emaciation and low growth rate | Lung consolidation, lymphadenopathy, and kidney necrosis | Positive | |
| 2 | 2A | No abnormality was found | No abnormality was found | Negative | 0% (0/5) |
| | 2B | No abnormality was found | No abnormality was found | Negative | |
| | 2C | No abnormality was found | No abnormality was found | Negative | |
| | 2D | No abnormality was found | No abnormality was found | Negative | |
| | 2E | No abnormality was found | No abnormality was found | Negative | |

The results showed that, for all the piglets in the challenge group, they all had a persistent high temperature of above 40.5° C. for 3 to 5 days, with loss of appetite, depression, rough hair coat, emaciation and low growth rate, necropsy results showed different levels of lung consolidation, lymphadenopathy, and kidney necrosis, and PCR detection of each viscera tissue confirmed that the porcine circovirus type 3 virus can be isolated again; while for the blank control group, no abnormality was found. The results showed that the porcine circovirus type 3 SG strain of the present disclosure can cause the onset of disease after being inoculated into the piglets.

Example 4 Preparation of Porcine Circovirus Type 3 SG Strain Antigen

The cultures of different passages of the porcine circovirus type 3 SG strain screened in Example 2 were inoculated into a monolayer of PK15 passage cells at 1% (V/V) of the amount of the liquid virus medium, and adsorbed at 37° C. for 30 minutes, then added with the cell maintenance solution and incubated at 37° C. The cells were observed 1 to 2 times a day, and the cells grew well. After the cells were cultured at 36 to 37° C. for 4 to 7 days, the cell cultures were harvested, and the harvested cell cultures were frozen and thawed 2-3 times, and the virus solution was harvested to determine the virus titer. The virus solution was filtered through a hollow fiber (0.5 µm to 2 µm) filter column to remove cell debris, and then inactivated by adding 0.1% to 0.2% formaldehyde solution at 37° C. for 24 hours, and the completely inactivated virus antigen was used for prepare vaccines.

Example 5 Preparation of Inactivated Vaccine Against Porcine Circovirus Type 3 SG Strain The inactivated antigen of the porcine circovirus type 3 SG strain prepared in Example 4 was slowly added to the water-soluble adjuvant gel adjuvant (SEPPIC, France), and the mixture was continuously stirred and mixed thoroughly for 12 minutes by an emulsifying machine at 800 rpm. The specific formulation of the vaccine is shown in Table 2.

TABLE 2

Formulation and contents of inactivated vaccines against porcine circovirus type 3 SG strain

| | Passages of culture of SG Strain | Content of antigen before inactivation ($TCID_{50}$/ml) | Gel adjuvant (V/V) |
|---|---|---|---|
| Vaccine 1 | 5 | $10^{5.0}$ | 10% |
| Vaccine 2 | | $10^{6.0}$ | 10% |
| Vaccine 3 | | $10^{7.0}$ | 10% |
| Vaccine 4 | 55 | $10^{5.0}$ | 10% |

Example 6 Immunogenicity Test of Inactivated Vaccine Against Porcine Circovirus Type 3 SG Strain 25 healthy piglets negative for PCV2, PCV3 antigen and antibody by ELISA, which were 28-30 days old, were randomly divided into 5 groups, 5 piglets/group, and were immunized with the inactivated vaccines against porcine circovirus type 3 SG strain prepared in Example 5. Groups 3 to 6 were immunized with vaccines 1 to 4, respectively, and group 7, as a control group, was not immunized. Each immunization group was injected with 2 ml/piglet of vaccine, and the control group was inoculated with 2 ml/piglet of DMEM medium. The piglets were challenged with $10^{5.0}$ $TCID_{50}$/piglet of porcine circovirus type 3 SG strain on day 28 after immunization. After the challenge, each piglet was observed continuously and evaluated according to their clinical symptoms, pathological changes and results of detection of virus. The detailed results are shown in Table 3.

TABLE 3

Results of immunogenicity test of inactivated vaccines against porcine circovirus type 3 SG strain

| Group | Clinical symptoms | Pathological changes | Detection of virus (positive rate) | Protection rate |
|---|---|---|---|---|
| 3 | No abnormality was found | No abnormality was found | 0% (0/5) | 100% (5/5) |
| 4 | No abnormality was found | No abnormality was found | 0% (0/5) | 100% (5/5) |
| 5 | No abnormality was found | No abnormality was found | 0% (0/5) | 100% (5/5) |
| 6 | No abnormality was found | No abnormality was found | 0% (0/5) | 100% (5/5) |
| 7 | Temperature increased to above 40.5° C. for 3-5 days, loss of appetite, depression, rough hair coat, emaciation and low growth rate | All showed different levels of lung consolidation, lymphadenopathy, kidney necrosis | 100% (5/5) | 0% (0/5) |

The results showed that the porcine circovirus type 3 SG strain inactivated vaccine could provide 100% (5/5) protection rate for piglets after immunization, while all control piglets were ill after the challenge. This shows that the inactivated vaccines against porcine circovirus type 3 SG strain provided by the disclosure can provide excellent protection.

Example 7 Broad-Spectrum Protection Test of Inactivated Vaccines Against Porcine Circovirus Type 3 SG Strain 50 healthy piglets negative for PCV2, PCV3 antigen and antibody by ELISA, which were 28-30 days old, were randomly divided into 10 groups, 5 piglets/group, and groups 8 to 12 were immunized with the inactivated vaccine 1 against porcine circovirus type 3 SG strain prepared in Example 5, groups 13-17, as control groups, were not immunized. Each of the immunization groups was injected with 2 ml/piglet of the vaccine, and each of the control groups was inoculated with 2 ml/piglet of DMEM medium. The challenge was carried out on day 28 after immunization, and groups 8 and 13 were challenged with the porcine circovirus type 3 HN12 virulent strain newly isolated from Henan Province, China; groups 9 and 14 were challenged with the porcine circovirus type 3 JS08 virulent strain newly isolated from Jiangsu Province, China; groups 10 and 15 were challenged with the porcine circovirus type 3 JL11 virulent strain isolated from Jilin Province, China; groups 10 and 15 were challenged with the porcine circovirus type 3 CQ04 virulent strain isolated from Chongqing City, China; groups 12 and 17 were challenged with the porcine circovirus type 3 GD05 virulent strain newly isolated from Guangdong Province, China; the dose for all immunizations was $10^{5.0}$ TCID$_{50}$/piglet. After the challenge, each piglet was continuously observed, and evaluated according to their clinical symptoms, pathological changes and detection of virus. The detailed results are shown in Table 4.

TABLE 4

Results of broad-spectrum protection test for inactivated vaccines against porcine circovirus type 3 SG strain

| Group | Clinical symptoms | Pathological changes | Detection of virus (positive rate) | Protection rate |
|---|---|---|---|---|
| 8 | No abnormality was found | No abnormality was found | 0% (0/5) | 100% (5/5) |
| 9 | No abnormality was found | No abnormality was found | 0% (0/5) | 100% (5/5) |
| 10 | No abnormality was found | No abnormality was found | 0% (0/5) | 100% (5/5) |
| 11 | No abnormality was found | No abnormality was found | 0% (0/5) | 100% (5/5) |
| 12 | No abnormality was found | No abnormality was found | 0% (0/5) | 100% (5/5) |
| 13 | Temperature increased to above 40.5° C. for 3-5 days, loss of appetite, depression, rough hair coat, emaciation and low growth rate | All showed different levels of lung consolidation, lymphadenopathy, kidney necrosis | 100% (5/5) | 0% (0/5) |
| 14 | Temperature increased to above 40.5° C. for 3-5 days, loss of appetite, depression, rough hair coat, emaciation and low growth rate | All showed different levels of lung consolidation, lymphadenopathy, kidney necrosis | 100% (5/5) | 0% (0/5) |
| 15 | Temperature increased to above 40.5° C. for 3-5 days, loss of appetite, depression, rough hair coat, emaciation and low growth rate | All showed different levels of lung consolidation, lymphadenopathy, kidney necrosis | 100% (5/5) | 0% (0/5) |
| 16 | Temperature increased to above 40.5° C. for 3-5 days, loss of appetite, depression, rough hair coat, emaciation and low growth rate | All showed different levels of lung consolidation, lymphadenopathy, kidney necrosis | 100% (5/5) | 0% (0/5) |

TABLE 4-continued

Results of broad-spectrum protection test for inactivated
vaccines against porcine circovirus type 3 SG strain

| Group | Clinical symptoms | Pathological changes | Detection of virus (positive rate) | Protection rate |
|---|---|---|---|---|
| 17 | Temperature increased to above 40.5° C. for 3-5 days, loss of appetite, depression, rough hair coat, emaciation and low growth rate | All showed different levels of lung consolidation, lymphadenopathy, kidney necrosis | 100% (5/5) | 0% (0/5) |

According to the results, for groups 13-17, the control groups, all piglets showed different levels of clinical symptoms such as temperature increased to above 40.5° C. for 3-5 days, loss of appetite, depression, rough hair coat, emaciation and low growth rate etc and all the necropsy showed different levels of lung consolidation, lymphadenopathy, kidney necrosis, and PCR detection of each viscera tissue confirmed that the porcine circovirus type 3 virus can be isolated again; while for groups 8-12, the immunization groups, after the challenge, no abnormal clinical symptoms were found, and no abnormalities were observed in all tissues and organs after necropsy, PCR detection was performed on each viscera tissue, indicating negative for PCV3.

The above results indicate that the inactivated vaccine against porcine circovirus type 3 SG strain provided by the present disclosure can provide effective and complete immune protection for pigs against challenge by porcine circovirus type 3 from different geographical sources, and from each viscera tissue, no PCV3 strain that was used in the challenge could be detected. The vaccine compositions of the present disclosure have a broad spectrum of immunogenicity and provide complete protection against varies of porcine circovirus type 3 from different geographic sources.

Example 8 Application Test of Inactivated Vaccines Against Porcine Circovirus Type 3 SG Strain In a domestic commercial farm, compared with the historical average values, the sow mortality rate increased by 9.4%, the conception rate decreased by 1.2%, and the rate of mummified fetuses was increased by 8.2%. Clinically, the affected sows showed symptoms of anorexia, multifocal papules, spots and dermatitis on the skin surface. Mummified fetuses of different gestational ages were found for aborted sows. 40 pregnant sows with clinical manifestations were randomly divided into two groups: group A, group B, 20 pigs/group, group A was an immunization group, which was immunized with inactivated vaccine 1 against porcine circovirus type 3 SG strain prepared in Example 5, and group B was a blank control group. The immunization group was injected with 2 ml/pig of vaccine, and the blank control group was inoculated with 2 ml/pig of DMEM medium. The results of sow fertility for the two groups were counted. These results are shown in Table 5.

TABLE 5

Statistical results of sow fertility

| Group | No. | Number of healthy piglets | Number of mummified fetuses | Number of weak piglets | Average number of healthy piglets born | Healthy rate |
|---|---|---|---|---|---|---|
| A | A-1 | 11 | 0 | 0 | 11.85 | 99.6% (237/238) |
|   | A-2 | 12 | 0 | 0 | | |
|   | A-3 | 11 | 0 | 0 | | |
|   | A-4 | 13 | 0 | 0 | | |
|   | A-5 | 11 | 0 | 0 | | |
|   | A-6 | 12 | 0 | 0 | | |
|   | A-7 | 12 | 0 | 0 | | |
|   | A-8 | 10 | 0 | 1 | | |
|   | A-9 | 11 | 0 | 0 | | |
|   | A-10 | 12 | 0 | 0 | | |
|   | A-11 | 12 | 0 | 0 | | |
|   | A-12 | 13 | 0 | 0 | | |
|   | A-13 | 13 | 0 | 0 | | |
|   | A-14 | 12 | 0 | 0 | | |
|   | A-15 | 12 | 0 | 0 | | |
|   | A-16 | 11 | 0 | 0 | | |
|   | A-17 | 12 | 0 | 0 | | |
|   | A-18 | 12 | 0 | 0 | | |
|   | A-19 | 12 | 0 | 0 | | |
|   | A-20 | 13 | 0 | 0 | | |
| B | B-1 | 8 | 1 | 3 | 7.7 | 66.1% (154/233) |
|   | B-2 | 9 | 1 | 2 | | |
|   | B-3 | 8 | 1 | 2 | | |
|   | B-4 | 9 | 1 | 1 | | |
|   | B-5 | 0 | 13 | 0 | | |
|   | B-6 | 9 | 1 | 3 | | |
|   | B-7 | 10 | 0 | 1 | | |
|   | B-8 | 8 | 1 | 3 | | |

TABLE 5-continued

Statistical results of sow fertility

| Group | No. | Number of healthy piglets | Number of mummified fetuses | Number of weak piglets | Average number of healthy piglets born | Healthy rate |
|---|---|---|---|---|---|---|
| | B-9 | 9 | 1 | 2 | | |
| | B-10 | 9 | 0 | 3 | | |
| | B-11 | 9 | 0 | 2 | | |
| | B-12 | 8 | 1 | 2 | | |
| | B-13 | 0 | 11 | 0 | | |
| | B-14 | 9 | 0 | 3 | | |
| | B-15 | 8 | 1 | 3 | | |
| | B-16 | 8 | 1 | 2 | | |
| | B-17 | 10 | 0 | 2 | | |
| | B-18 | 9 | 0 | 2 | | |
| | B-19 | 7 | 1 | 3 | | |
| | B-20 | 7 | 2 | 3 | | |

The results showed that the immunization groups had no abnormality in fertility, producing healthy piglets with an average of 11.85 piglets/litter, and the healthy rate was as high as 99.6%. However, the control group showed obvious mummified fetuses and weak piglets, and the average number of healthy piglets was 7.7 per litter, and the healthy rate was 66.1%, and two sows aborted with the whole litter having mummified fetuses. The difference between the immunization groups and the control groups was significant.

The results in Table 5 demonstrate that the inactivated vaccine of the porcine circovirus type 3 SG strain of the present disclosure has a good immunoprotective effect on sows infected with porcine circovirus type 3, and can protect sows which have been infected with PCV3.

At the same time, the piglets produced from the control group B were isolated and feed by litter, and 18 litters were divided into two groups: group B1 (a total of 15 litters of piglets, including litters B-1 to B-17, except litters B-5 and B-13 due to the whole litter having mummified fetuses), group B2 (a total of 3 litters, including litters B-18 to B-20), the piglets in group B1 were immunized with inactivated vaccine 1 against porcine circovirus type 3 SG strain prepared in Example 5 before breastfeeding, group B2 was a blank control group. The immunization group was injected with 2 ml/piglet of vaccine, and the blank control group was inoculated with 2 ml/piglet of DMEM medium. Each piglet was continuously observed and judged according to the clinical symptoms, pathological changes and virus detection of each piglet. The detailed results are shown in Table 6.

TABLE 6

Immune protection test of inactivated vaccine against porcine circovirus type 3 SG strain on piglets

| Group | | clinical symptoms | pathological changes | detection of virus (positive rate) | protection rate |
|---|---|---|---|---|---|
| B1 | B-1 | No abnormality was found | No abnormality was found in necropsy of one randomly selected piglet | The tissue sample from the piglet subjected to necropsy was determined as negative | 100% (8/8) |
| | B-2 | No abnormality was found | No abnormality was found in necropsy of one randomly selected piglet | The tissue sample from the piglet subjected to necropsy was determined as negative | 100% (9/9) |
| | B-3 | No abnormality was found | No abnormality was found in necropsy of one randomly selected piglet | The tissue sample from the piglet subjected to necropsy was determined as negative | 100% (8/8) |
| | B-4 | No abnormality was found | No abnormality was found in necropsy of one randomly selected piglet | The tissue sample from the piglet subjected to necropsy was determined as negative | 100% (9/9) |
| | B-6 | No abnormality was found | No abnormality was found in necropsy of one randomly selected piglet | The tissue sample from the piglet subjected to necropsy was determined as negative | 100% (9/9) |

TABLE 6-continued

Immune protection test of inactivated vaccine against porcine circovirus type 3 SG strain on piglets

| | Group | clinical symptoms | pathological changes | detection of virus (positive rate) | protection rate |
|---|---|---|---|---|---|
| | B-7 | No abnormality was found | No abnormality was found in necropsy of one randomly selected piglet | The tissue sample from the piglet subjected to necropsy was determined as negative | 100% (10/10) |
| | B-8 | No abnormality was found | No abnormality was found in necropsy of one randomly selected piglet | The tissue sample from the piglet subjected to necropsy was determined as negative | 100% (8/8) |
| | B-9 | No abnormality was found | No abnormality was found in necropsy of one randomly selected piglet | The tissue sample from the piglet subjected to necropsy was determined as negative | 100% (9/9) |
| | B-10 | No abnormality was found | No abnormality was found in necropsy of one randomly selected piglet | The tissue sample from the piglet subjected to necropsy was determined as negative | 100% (9/9) |
| | B-11 | No abnormality was found | No abnormality was found in necropsy of one randomly selected piglet | The tissue sample from the piglet subjected to necropsy was determined as negative | 100% (9/9) |
| | B-12 | No abnormality was found | No abnormality was found in necropsy of one randomly selected piglet | The tissue sample from the piglet subjected to necropsy was determined as negative | 100% (8/8) |
| | B-14 | No abnormality was found | No abnormality was found in necropsy of one randomly selected piglet | The tissue sample from the piglet subjected to necropsy was determined as negative | 100% (9/9) |
| | B-15 | No abnormality was found | No abnormality was found in necropsy of one randomly selected piglet | The tissue sample from the piglet subjected to necropsy was determined as negative | 100% (8/8) |
| | B-16 | No abnormality was found | No abnormality was found in necropsy of one randomly selected piglet | The tissue sample from the piglet subjected to necropsy was determined as negative | 100% (8/8) |
| | B-17 | No abnormality was found | No abnormality was found in necropsy of one randomly selected piglet | The tissue sample from the piglet subjected to necropsy was determined as negative | 100% (10/10) |
| B2 | B-18 | Temperature increased to above 40.5° C. for 3-5 days, loss of appetite, depression, rough hair coat, emaciation and low growth rate; 4 piglets died. | All showed different levels of lung consolidation, lymphadenopathy, kidney necrosis | 100% (9/9) | 0% (0/9) |
| | B-19 | Temperature increased to above 40.5° C. for 3-5 days, loss of appetite, depression, rough hair coat, emaciation and low growth rate; 2 piglets died. | All showed different levels of lung consolidation, lymphadenopathy, kidney necrosis | 100% (7/7) | 0% (0/7) |

TABLE 6-continued

Immune protection test of inactivated vaccine against porcine circovirus type 3 SG strain on piglets

| Group | clinical symptoms | pathological changes | detection of virus (positive rate) | protection rate |
|---|---|---|---|---|
| B-20 | Temperature increased to above 40.5° C. for 3-5 days, loss of appetite, depression, rough hair coat, emaciation and low growth rate; 3 piglets died. | All showed different levels of lung consolidation, lymphadenopathy, kidney necrosis | 100% (7/7) | 0% (0/7) |

According to the results, for the immunization group, no abnormal clinical symptoms were found, and no abnormalities were observed in all tissues and organs after necropsy, PCR detection was performed on each viscera tissue of piglets, indicating negative for PCV3; while for the piglets in the control group, they all showed different levels of clinical symptoms such as temperature increased to above 40.5° C. for 3-5 days, loss of appetite, depression, rough hair coat, emaciation and low growth rate etc, a part of piglets died, and all the necropsy showed different levels of pathological changes like lung consolidation, lymphadenopathy, and kidney necrosis, and PCR detection of each viscera tissue confirmed that the porcine circovirus type 3 virus can be isolated again;

Since PCV3 can be vertically transmitted in the herd, the results in Table 6 demonstrate that the inactivated vaccine of the porcine circovirus type 3 SG strain in the present disclosure has a good immunoprotective effect on piglets infected with porcine circovirus type 3, and can also protect piglets that have been infected with PCV3 with a protection rate of 100%.

The foregoing descriptions are merely preferred examples of the present disclosure and are not intended to limit the present disclosure in any form. Although the present disclosure has been disclosed by way of preferred examples, it is to be understood that the disclosure is not limited thereto. A person skilled in the art can make some equivalent variations or modifications to the above-disclosed technical content without departing from the scope of the technical solutions of the present disclosure to obtain equivalent examples. Simple modifications, equivalent changes and modifications made to the above examples according to the technical essence of the present disclosure all fall within the scope of the technical solutions of the present disclosure without departing from the contents of the technical solutions of the present disclosure.

The invention claimed is:

1. A vaccine composition, wherein the vaccine composition comprises an immunogenic amount of inactivated antigen of the porcine circovirus type 3 SG strain or a culture thereof, and an adjuvant, and wherein the porcine circovirus type 3 SG strain has the accession number CCTCC NO. V201712 deposited at the China Center for Type Culture Collection.

2. The vaccine composition according to claim 1, wherein the inactivated antigen of the porcine circovirus type 3 SG strain or the culture thereof is an inactivated whole-virus antigen of the porcine circovirus type 3 virus SG strain or the culture thereof.

3. The vaccine composition according to claim 2, wherein the inactivated whole-virus antigen content of the porcine circovirus type 3 SG strain or the culture thereof is equal to or more than $10^{5.0}$ $TCID_{50}$/ml before inactivation.

4. The vaccine composition according to claim 2, wherein the inactivated whole-virus antigen content of the porcine circovirus type 3 SG strain or the culture thereof is within a range of $10^{5.0}$ to $10^{7.0}$ $TCID_{50}$/ml before inactivation.

5. The vaccine composition according to claim 2, wherein the inactivated whole-virus antigen content of the porcine circovirus type 3 SG strain or the culture thereof is $10^{6.0}$ $TCID_{50}$/ml before inactivation.

6. The vaccine composition according to claim 1, wherein the culture of the porcine circovirus type 3 SG strain is a culture which has been subcultured for more than one passage.

7. The vaccine composition according to claim 6, wherein the culture of the porcine circovirus type 3 SG strain is a culture which has been subcultured for more than five passages.

8. The vaccine composition according to claim 7, wherein the culture of the porcine circovirus type 3 SG strain is a culture which has been subcultured for 5 to 55 passages.

9. The vaccine composition according to claim 1, wherein the adjuvant comprises white oil, and other animal oils, vegetable oils or mineral oil; or aluminum hydroxide, aluminum phosphate, and other metal salts; or a polymer-based adjuvant which contains gel particles of sodium polyacrylate in water, carbomer, squalane or squalene, ISA206 adjuvant, saponin, oil emulsion, oil in water emulsions, water-in-oil emulsion.

10. The vaccine composition according to claim 9, wherein the adjuvant is used in an amount of 5 to 20% by volume.

11. The vaccine composition according to claim 10, wherein the adjuvant is used in an amount of 10% by volume.

12. A method for prevention and/or treatment of porcine circovirus type 3 related diseases by administration of an effective amount of the vaccine composition of claim 1 to a subject.

* * * * *